(12) United States Patent
Prencipe et al.

(10) Patent No.: US 8,501,161 B2
(45) Date of Patent: Aug. 6, 2013

(54) ORAL CARE REGIMEN

(75) Inventors: Michael Prencipe, Princeton Junction, NJ (US); Isabelle Van Rycke, Paris (FR); Richard Lovell, Le Vesinet (FR)

(73) Assignee: Colgate-Palmolive Company, New York, NY (US)

( * ) Notice: Subject to any disclaimer, the term of this patent is extended or adjusted under 35 U.S.C. 154(b) by 1511 days.

(21) Appl. No.: 11/745,158

(22) Filed: May 7, 2007

(65) Prior Publication Data

US 2007/0286820 A1 Dec. 13, 2007

Related U.S. Application Data

(60) Provisional application No. 60/798,940, filed on May 9, 2006.

(51) Int. Cl.
*A61K 8/00* (2006.01)

(52) U.S. Cl.
USPC .................................. 424/49; 424/52

(58) Field of Classification Search
None
See application file for complete search history.

(56) References Cited

U.S. PATENT DOCUMENTS

| | | |
|---|---|---|
| 3,538,230 A | 11/1970 | Pader et al. |
| 3,862,307 A | 1/1975 | DiGiulio |
| 3,925,543 A | 12/1975 | Donohue |
| 3,932,605 A | 1/1976 | Vit |
| 3,932,608 A | 1/1976 | Anderson et al. |
| 3,943,241 A | 3/1976 | Anderson et al. |
| 3,988,434 A | 10/1976 | Schole et al. |
| 4,011,309 A | 3/1977 | Lutz |
| 4,022,880 A | 5/1977 | Vinson et al. |
| 4,025,616 A | 5/1977 | Haefele |
| 4,042,680 A | 8/1977 | Muhler et al. |
| 4,064,138 A | 12/1977 | Saari et al. |
| 4,100,269 A | 7/1978 | Pader |
| 4,108,979 A | 8/1978 | Muhler et al. |
| 4,108,981 A | 8/1978 | Muhler et al. |
| 4,146,607 A | 3/1979 | Ritchey |
| 4,154,813 A | 5/1979 | Kleinberg |
| 4,160,821 A | 7/1979 | Sipos |
| 4,216,961 A | 8/1980 | McQuillan |
| 4,225,579 A | 9/1980 | Kleinberg |
| 4,259,316 A | 3/1981 | Nakashima et al. |
| 4,269,822 A | 5/1981 | Pellico et al. |
| 4,305,928 A | 12/1981 | Harvey |
| 4,335,102 A | 6/1982 | Nakashima et al. |
| 4,339,432 A | 7/1982 | Ritchey et al. |
| 4,340,583 A | 7/1982 | Wason |
| RE31,181 E | 3/1983 | Kleinberg |
| 4,466,954 A | 8/1984 | Ichikawa et al. |
| 4,528,181 A | 7/1985 | Morton et al. |
| 4,532,124 A | 7/1985 | Pearce |
| 4,538,990 A | 9/1985 | Pashley |
| 4,645,662 A | 2/1987 | Nakashima et al. |
| 4,656,031 A | 4/1987 | Lane et al. |
| 4,721,614 A | 1/1988 | Winston et al. |
| 4,725,576 A | 2/1988 | Pollock et al. |
| 4,894,220 A | 1/1990 | Nabi et al. |
| 4,986,981 A | 1/1991 | Glace et al. |
| 4,997,640 A | 3/1991 | Bird et al. |
| 5,037,635 A | 8/1991 | Nabi et al. |
| 5,080,887 A | 1/1992 | Gaffar et al. |
| 5,096,700 A | 3/1992 | Seibel et al. |
| 5,156,835 A | 10/1992 | Nabi et al. |
| 5,286,480 A | 2/1994 | Boggs et al. |
| 5,288,480 A | 2/1994 | Gaffar et al. |
| 5,292,526 A | 3/1994 | Gaffar et al. |

(Continued)

FOREIGN PATENT DOCUMENTS

| | | |
|---|---|---|
| EP | 0 569 666 A | 11/1993 |
| GB | 2235133 | 2/1991 |

(Continued)

OTHER PUBLICATIONS

International Search Report Dated (Oct. 2, 2008).

(Continued)

*Primary Examiner* — Brian Gulledge
*Assistant Examiner* — Snigdha Maewall
(74) *Attorney, Agent, or Firm* — Howard C. Lee

(57) ABSTRACT

The invention includes methods of cleaning an oral surface, maintaining oral health and/or increasing oral health. Such methods encompass contacting an oral surface with a primary oral care composition at least once daily, and contacting the oral surface with a periodic oral care composition at least once within a period of about 42 days. The periodic oral care compositions suitable for use in the method comprise a first abrasive having an Einlehner hardness of greater than about 5 mg loss per 100,000 revolutions and a second abrasive having an Einlehner hardness of less than about 5 mg loss per 100,000 revolutions. In the periodic oral care compositions, the ratio of the first abrasive to the second abrasive is about 1:1.6 to about 1.6:1. The periodic oral care compositions are characterized by a pellicle cleaning ratio of greater than about 100 and a radioactive dentin abrasion of less than about 200. Additionally or alternatively, the methods may include those where the second abrasive comprises silica and has an oil of absorption of greater than about 90 $cm^3/100$ g and/or an Einlehner hardness of less than about 5 mg loss per 100,000 revolutions. The ratio of the first abrasive to the second abrasive may be about 1:1.6 to about 1.6:1. The total amount of the first and second abrasives present in the oral composition may be greater than about 25% by weight of the composition and/or the oral composition has a pellicle cleaning ratio of greater than about 100 and a radioactive dentin abrasion of less than about 200.

16 Claims, No Drawings

U.S. PATENT DOCUMENTS

| | | | |
|---|---|---|---|
| 5,334,617 | A | 8/1994 | Ulrich et al. |
| 5,344,641 | A | 9/1994 | Gaffar et al. |
| 5,356,615 | A | 10/1994 | Gaffar |
| 5,370,865 | A | 12/1994 | Yamagishi et al. |
| 5,538,715 | A | 7/1996 | Gaffar et al. |
| 5,589,160 | A | 12/1996 | Rice |
| 5,639,795 | A | 6/1997 | Friedman et al. |
| 5,747,004 | A | 5/1998 | Giani et al. |
| 5,762,911 | A | 6/1998 | Kleinberg et al. |
| 5,776,435 | A | 7/1998 | Gaffar et al. |
| 5,906,811 | A | 5/1999 | Hersh |
| 5,922,346 | A | 7/1999 | Hersh |
| 5,939,051 | A | 8/1999 | Santalucia et al. |
| 5,997,301 | A | 12/1999 | Linden |
| 6,217,581 | B1 | 4/2001 | Tolson |
| 6,290,933 | B1 * | 9/2001 | Durga et al. ............... 424/49 |
| 6,379,654 | B1 | 4/2002 | Gebreselassie et al. |
| 6,436,370 | B1 | 8/2002 | Kleinberg et al. |
| 6,488,961 | B1 | 12/2002 | Robinson et al. |
| 6,524,558 | B2 | 2/2003 | Kleinberg et al. |
| 6,558,654 | B2 | 5/2003 | McLaughlin |
| 6,669,929 | B1 | 12/2003 | Boyd et al. |
| 6,685,921 | B2 | 2/2004 | Lawlor |
| 6,850,883 | B1 | 2/2005 | Kapanen et al. |
| 2002/0081360 | A1 | 6/2002 | Burgard et al. |
| 2004/0126332 | A1 | 7/2004 | Boyd et al. |
| 2004/0136924 | A1 | 7/2004 | Boyd et al. |
| 2005/0019273 | A1 | 1/2005 | Boyd et al. |
| 2005/0271601 | A1 | 12/2005 | Milanovich et al. |
| 2005/0271602 | A1 | 12/2005 | Milanovich et al. |
| 2006/0002865 | A1 | 1/2006 | Buelo |
| 2006/0216247 | A1 | 9/2006 | Phillips |
| 2007/0140986 | A1 | 6/2007 | Prencipe et al. |

FOREIGN PATENT DOCUMENTS

| | | | |
|---|---|---|---|
| GB | 2263066 | | 7/1993 |
| JP | H8-151324 | | 6/1996 |
| WO | 9732565 | A | 9/1997 |
| WO | 9943291 | A | 9/1999 |
| WO | 0078270 | A | 12/2000 |
| WO | 0185115 | A | 11/2001 |
| WO | 0234213 | A | 5/2002 |
| WO | 2004043419 | A | 5/2004 |
| WO | WO 2004/054529 | | 7/2004 |
| WO | WO 2004/054531 | | 7/2004 |
| WO | 2007094891 | A | 8/2007 |
| WO | WO 2007/117498 | | 10/2007 |
| WO | WO 2007/134003 | | 11/2007 |
| WO | WO 2009/099450 | | 8/2009 |

OTHER PUBLICATIONS

International Search Report PCT/US2008/058650 Dated Jan. 5, 2009.
English Translation of Official Action issued in Russian Application No. 2008148329 mailed on Mar. 11, 2010.
Kratkaya meditsiskaya encyklopediya, Acad.RAMN, V.I. Pocrovsky, t.II, M, 1994, p. 284.
U.S. Appl. No. 07/398,605, filed Aug. 25, 1989, specification.
Acevedo et al., 2005, "The Inhibitory Effect of an Arginine Bicarbonate/Calcium Carbonate (CaviStat®)-Containing Dentifrice on the Development of Dental Caries in Venezuaelan School Children," J. Clinical Dentistry 16(3):63-70.
American Dental Association, 2007, "Cleaning Your Teeth and Gums (Oral Hygiene)," Oral Health Topics A-Z.
Chatterjee et al., 2005, "Bacterial Acidification and CaviStat® Alkalinization of Occlusal Fissure pH," 83rd Session of the American Assoc. For Dental Research, Mar. 9-12, Abstract.
DenClude Packaging with Ingredient List, 2004.
Kleinberg, 1999, "A New Saliva-Based Anticaries Composition," Dentistry Today 18(2):98-103.
Kleinberg, 2002, "A Mixed-Bacteria Ecological Approach to Understanding the Role of the Oral Bacteria in Dental Caries Casuation: An Alternative to *Streptococcus mutans* and the Specific-Plaque Hypothesis," Crit. Rev. Oral Biol. Med. 12(2):108-125.
Machado et al., 2007, "CaviStat Confection Inhibition of Caries in Posterior Teeth," 83rd Session of the American Assoc. for Dental Research, Mar. 21-24, Abstract.
ProClude Packaging with Ingredient List, 2002.
Silverman et al., 2006, "Antimicrobial Mouthrinse as Part of a Comprehensive Oral Care Regimen," J. American Dental Assoc. 137(3):22S-26S.
U.S. Appl. No. 60/752,340.
Yahoo! Shopping, 2007, Reach Oral Care Search Results.

* cited by examiner

ORAL CARE REGIMEN

CROSS REFERENCE TO RELATED APPLICATION

This application claims priority to U.S. Provisional Patent application Ser. No. 60/798,940 filed May 9, 2006, the contents of which are incorporated herein by reference.

BACKGROUND OF THE INVENTION

Consumers report perceptions of refreshment, contentment, cleanliness, and general well-being similar to those experienced post-spa or beauty treatment after a professional teeth cleaning carried out by a dentist or hygienist. Thus, there is a need in the art for an at-home oral care regiment that permits consumers to re-create the "extra clean" mouth feel and associated sense of well-being experienced after a professional teeth cleaning.

BRIEF SUMMARY OF THE INVENTION

The invention includes methods of cleaning an oral surface, maintaining oral health and/or increasing oral health. Such methods encompass contacting an oral surface with a primary oral care composition at least once daily, and contacting the oral surface with a periodic oral care composition at least once within a period of about 42 days. The periodic oral care compositions suitable for use in the method comprise a first abrasive having an Einlehner hardness of greater than about 5 mg loss per 100,000 revolutions and a second abrasive having an Einlehner hardness of less than about 5 mg loss per 100,000 revolutions. In the periodic oral care compositions, the ratio of the first abrasive to the second abrasive is about 1:1.6 to about 1.6:1. The periodic oral care compositions are characterized by a pellicle cleaning ratio of greater than about 100 and a radioactive dentin abrasion of less than about 200. Additionally or alternatively, the methods may include those where the second abrasive comprises silica and has an oil of absorption of greater than about 90 $cm^3$/100 g and/or an Einlehner hardness of less than about 5 mg loss per 100,000 revolutions. The ratio of the first abrasive to the second abrasive may be about 1:1.6 to about 1.6:1. The total amount of the first and second abrasives present in the oral composition may be greater than about 25% by weight of the composition and/or the oral composition has a pellicle cleaning ratio of greater than about 100 and a radioactive dentin abrasion of less than about 200.

DETAILED DESCRIPTION OF THE INVENTION

The invention provides a regimen method of cleaning an oral surface to remove, for example, bacteria, food particles, biofilm, plaque, and/or other agents that may result in or contribute to various oral conditions, such as bad breath, poor oral health, gingivitis, gum inflammation, or periodontitis. The regimen method of the invention also provides the user with a smooth, polished feel and appearance to the tooth surfaces that may be perceived as comparable to the "clean feel" experienced after a professional cleaning. Methods of maintaining oral health and/or increasing oral health are also provided.

The invention is an oral care regimen that includes contacting an oral surface with at least two oral care compositions at differing time increments. The oral surface to be treated includes any within the oral cavity. Exemplary surfaces include hard tissues (e.g., teeth) and soft surfaces (e.g., gingiva and tongue).

One of the oral care compositions used in the regimen method of the invention is a primary oral care composition. The primary oral care composition may be any known or to be developed in the art and can take any form. For example, the primary oral care composition may be in the form of a rinse, paste, gel, fluid, suspension, film, patch, gum, lozenge, confectionary, or semi-solid pates or stick. The primary oral care composition may be a conventional toothpaste, such as those as those sold under the COLGATE® trademark (Colgate-Palmolive Company, New York, N.Y.) or under the CREST® trademark (Procter & Gamble Corporation, Cincinnati, Ohio). Alternatively, the primary oral care composition may be any of those described in, e.g., U.S. Pat. Nos. 4,721,614; 4,894,220; 4,986,981; 5,037,635; 5,156,835; 5,288,480; 5,344,641; 5,538,715; 5,776,435 and U.S. Patent Application Publication Nos. 2004/0126332, 2004/0136924, 2005/0019273, 2005/0271601, and 2005/0271602, the contents of each of which are incorporated herein by reference.

The primary oral care composition may contain one or more agents such as humectants, solvents, thickeners, surfactants, abrasives, flavorants, colorants, viscosity and/or rheology modifiers, gums, polymers, sweeteners, etc. Examples of agents that may be present in the primary oral care composition include an antibacterial agent, a plaque dispersion agent, an antiadhesion agent, an anticaries agent, a desensitizing agent, a flavorant, a colorant, a stannous ion agent, triclosan, triclosan monophosphate, chlorhexidine, alexidine, hexetidine, sanguinarine, benzalkonium chloride, salicylanilide, domiphen bromide, cetylpyridinium chloride, tetradecylpyridinium chloride, N-tetradecyl-4-ethylpyridinium chloride, octenidine, delmopinol, octapinol, nisin, zinc ion agent, copper ion agent, essential oils, furanones, bacteriocins, ethyl lauroyl arginate, extracts of magnolia, a metal ion source, arginine bicarbonate, honokiol, magonol, ursolic acid, ursic acid, morin, extract of sea buckthorn, a peroxide, an enzyme, a Camellin extract, a flavonoid, a flavan, halogenated diphenyl ether, creatine, and/or propolis.

In the practice of the methods of the invention, the primary oral care composition may be applied or contacted to the oral surface at least once daily. In some embodiments, the application of the primary oral care composition may be carried out two, three, four, five, six, seven times daily, or up to fifteen times daily.

The oral surface may be contacted to the primary oral care composition using any means known or to be developed in the art; such means may vary depending on the form of the primary oral care composition. Exemplary means of contacting the primary oral care composition to the oral surface include application using an implement (such as a brush, toothbrush, stick, sponge, cotton swab), lavage, chewing, adjacent placement, and dissolution of confectionary.

Another of the oral care composition used in the methods of the invention is a periodic oral care composition. The periodic oral care composition has a Pellicle Cleaning Ratio ("PCR") of greater than 100, while having a Radiotracer Dentin Abrasion ("RDA") of less than 200. In certain embodiments, the RDA is less than or equal to about 175, while still having a PCR that exceeds about 100. In some embodiments, the RDA is less than 165. (Methods of performing PCR and RDA are described in e.g., U.S. Pat. Nos. 5,939,051 and 6,290,933, both of which are herein incorporated by reference in their entireties.)

The periodic oral care composition includes a first abrasive and a second abrasive; such abrasives are described in U.S.

Patent Application Ser. No. 60/752,340, filed Dec. 21, 2005, the contents of which are incorporated herein by reference.

In certain embodiments, the periodic oral composition comprises a first abrasive having an Einlehner hardness of greater than about 5 mg loss per 100,000 revolutions and a second abrasive having an Einlehner hardness of less than about 5 mg loss per 100,000 revolutions. The first particle having an Einlehner hardness of greater than 5 mg loss per 100,000 revolutions has a primary a polishing function when it is contacted with an oral surface. The second particle having an Einlehner hardness of less than about 5 mg loss per 100,000 revolutions has a primary cleaning function, as it is a softer particle. In certain embodiments, the second particle has a hardness of greater than about 10 mg loss per 100,000 revolutions, and in other embodiments, greater than about 15 mg loss per 100,000 revolutions.

The first abrasive of the periodic oral care composition may be of a cleaning abrasive that has a hardness of less than or equal to the oral surface to be treated, and the second abrasive is a polishing abrasive that has a hardness of greater than or equal to the oral surface to be treated.

Each of the first abrasive and second abrasive of the periodic oral care composition has a particle size. In certain embodiments, the first particle size is less than the second particle size. Mean particle size can be measured, e.g., using a Malvern Particle Size Analyzer, Model Mastersizer S, Malvern Instruments, Inc. of Southborough, Mass., U.S.A.

In certain embodiments, the first abrasive has a mean particle size of less than about 11 µm, preferably less than about 10 µm. For example, examples of suitable abrasives have mean particle sizes ranging from about 7 µm to 11 µm. Some abrasives have particle sizes of less than 5 µm. In other embodiments, the second abrasive has a mean particle size of greater than about 8 µm, preferably greater than about 10 µm. In some embodiments, the second abrasive can have a mean particle size of about 8 µm to about 14 µm.

Any orally or cosmetically acceptable abrasive fulfilling the requirements set forth above can be selected for use in the periodic oral care composition. Suitable abrasives include without limitation, silica, silicate, silicon, alumina (including calcined aluminum oxide), aluminosilicates, such as bentonite, zeolite, kaolin, and mica, siliceous or diatomaceous earth, pumice, calcium carbonate, cuttlebone, insoluble phosphates, composite resins, such as melamine resin, phenolic resin, and urea-formaldehyde resin, polycarbonate, silicon carbide, boron carbide, microcrystalline wax, microcrystalline cellulose, including combinations of colloidal microcrystalline cellulose and carboxymethylcellulose, commercially available under the trade name AVICEL® from FMC Biopolymer of Philadelphia, Pa., U.S.A, and combinations and derivatives of all of the above. By "mica" it is meant any one of a group of hydrous aluminum silicate minerals with plate morphology and perfect basal (micaceous) cleavage. Mica can be, for example, sheet mica, scrap mica or flake mica, as exemplified by muscovite, biotite or phlogopite type micas. Among insoluble phosphates useful as abrasives are orthophosphates, polymetaphosphates and pyrophosphates. Illustrative examples are dicalcium orthophosphate dihydrate, dicalcium phosphate dihydrate, calcium hydrogen phosphate, calcium pyrophosphate, P-calcium pyrophosphate, tricalcium phosphate, calcium metaphosphate, potassium metaphosphate, and sodium metaphosphate.

Synthetic silicas include both silica gels and precipitated silicas which may be prepared, for example, by the neutralization of aqueous silicate solutions with a strong mineral acid. In the preparation of silica gel, a silica hydrogel is formed which is then typically washed to low salt content. The washed hydrogel may be milled to the desired size, or otherwise dried, ultimately to the point where its structure no longer changes as a result of shrinkage. When preparing such synthetic silicas, the objective is to obtain abrasives which provide maximal cleaning (i.e., removal of stained pellicle) with minimal damage to the tooth enamel and other oral tissue Useful abrasive materials for preparing the periodic oral compositions include high cleaning, low structure silica abrasives, such as those marketed under the trade designation SYLODENT® XWA or SYLODENT® 783 by Davison Chemical Division of W. R. Grace & Co. of Baltimore, Md. SYLODENT® XWA 650 is a silica hydrogel composed of particles of colloidal silica. Exemplary silica hydrogels comprise colloidal particles of silica having an average particle size of about 3 µm to about 12 µm, and more preferably between about 5 µm to about 10 µm, with a pH range from 4 to 10, preferably 6 to 9 when measured as a 5% by weight slurry. The particles of the XWA 650 contain about 10% to about 35% by weight water, have a mean particle size of about 5 µm to about 12 µm, an Einlehner hardness of from greater than or equal to about 5 to about 20 mg loss per 100,000 revolutions, an oil absorption of less than 90 cm$^3$/100 g, for example from between about 40 cm$^3$/100 g to about 90 cm$^3$/100 g. The abrasives have a Brunauer, Emmett and Teller (BET) surface area from 100 to 700 m$^2$/g. XWA 650 has a brightness of 96.8 technidyne. Such abrasives are disclosed in, e.g. U.S. Pat. No. 6,290,933, which is incorporated herein by reference in its entirety.

Another high cleaning silica abrasive that can be included in the periodic composition is marketed as SYLODENT® XWA 300 and is a silica hydrogel containing about 10% to about 25% water by weight, where the mean particles size is about 2 µm to about 4 µm. The particles have BET surface are in the range of 150 to 400 m$^2$/g of silica. The XWA 300 abrasive has an oil absorption of less than 90 cm$^3$/100 g silica; and a pH, in a 5% w/w suspension in boiled ($CO_2$ free) demineralized water, equal to or greater than 8.5. Such abrasives are disclosed in U.S. Pat. No. 5,939,051, which is incorporated herein by reference in its entirety.

Another suitable high cleaning silica that can be included in the periodic composition comprises a silica product, where the particles are about 5% to about 35% by weight water, having a mean particle size of about 7 µm to about 11 µm, an Einlehner hardness of from 12 to about 19, an oil absorption value of about 50 cm$^3$/100 g to about 65 cm$^3$/100 g. A BET surface area is about 100 to about 700 m$^2$/g of silica. The brightness is generally reported to be greater than about 95 technidyne. Such a silica product is commercially available as ZEODENT® 105 from J. M. Huber of Havre de Grace, Maryland, U.S.A.

Other abrasives that can be used include typical cleaning silica abrasives, such as precipitated silicas having a mean particle size of up to about 20 µm, typically at about 8 to about 14 µm, with an oil absorption structure of greater than about 90 to about 110 cm$^3$/100 g, such as ZEODENT®115, marketed by J. M. Huber, that has a pH at 5% of the particles of about 6.5-7.5 and an Einlehner hardness of about 2 to 4 mg loss per 100,000 revolutions. The brightness of such a silica particle is greater than about 95. Such cleaning abrasives comprise the second abrasive of the oral composition in certain embodiments.

In embodiments where the dentifrice is a clear or transparent gel, an abrasive of colloidal silica, such as those sold under the trademark SYLOID® as SYLOID® 72 and SYLOID® 74 or under the trademark SANTOCEL® 100 alkali metal alumina-silicate complexes are particularly useful, since they have refractive indices close to the refractive indices of gelling agent-liquid (including water and/or humectant) systems commonly used in dentifrices.

In accordance with various embodiments of the present invention, a first and a second abrasive are combined in the periodic composition to provide cleaning capability, mildness (relatively low abrasivity), and aesthetically acceptable periodic care compositions. In various embodiments, an amount of the first abrasive to the second abrasive can be expressed by a ratio of the first abrasive to the second abrasive ranging from about 1:1.6 to about 1.6:1. For example, a ratio of the first abrasive to the second abrasive is about 1:1. The respective amounts of the first abrasive and the second abrasive present in an oral composition may be about 13 to about 21% by weight of the oral composition.

In some embodiments, the amount of the first abrasive is about 15% to about 19%, and the amount of the second abrasive is about 15% to about 19% by weight of the oral composition. In certain preferred embodiments, the first abrasive is present at about 17% by weight and the second abrasive is present at about 17% by weight of the oral composition. Thus, in accordance with various embodiments of the present invention, the total amount of abrasive in the periodic oral care composition, including the first and second abrasive is preferably greater than about 25%, even more preferably greater than about 30%, and in some embodiments, greater than about 35% by total weight of the periodic oral care composition.

In some embodiments, the periodic oral composition comprises a first abrasive having an Einlehner hardness of greater than about 5 mg loss per 100,000 revolutions and a second abrasive having an Einlehner hardness of less than about 5 mg loss per 100,000 revolutions. A ratio of the first abrasive to the second abrasive ranges from about 1:1.6 to about 1.6:1. Further, the periodic oral composition has a PCR of greater than about 100 and an RDA of less than about 200. In certain embodiments, the RDA is less than about 175. In certain embodiments, the first abrasive has an oil of absorption of less than about 90 cm$^3$/100 g, and the second abrasive has an oil of absorption of greater than about 90 cm$^3$/100 g. In some embodiments, the ratio of the first abrasive to the second abrasive is about 1:1. The total amount of the abrasives, including both the first and the second abrasives, is greater than about 30%. The first abrasive and the second abrasive are optionally present at about 17% each, respectively. In some embodiments, the first and second abrasives are respectively present in an amount of about 15% to about 19% by weight of the total periodic oral care composition. The first and second abrasives optionally comprise silica.

In certain embodiments, the periodic oral composition comprises a first abrasive comprising silica, having an Einlehner hardness of greater than about 5 mg loss per 100,000 revolutions, and an oil of absorption of less than about 90 cm$^3$/100 g. The periodic oral composition further comprises a second abrasive comprising silica having an Einlehner hardness of less than about 5 mg loss per 100,000 revolutions, and an oil of absorption of greater than about 90 cm$^3$/100 g. The first abrasive is present at an amount of about 13% to about 21% by weight, likewise, the second abrasive is present in an amount of about 13% to about 21% by weight of the composition. In some embodiments, the first abrasive and the second abrasive are respectively present at about 15% to about 19% by weight of the periodic oral composition. In certain embodiments, the first and second abrasives are respectively present in an amount of about 17% by weight of the oral composition. The PCR is preferably greater than 100 and the RDA is preferably less than 200, and in certain embodiments, less than about 175. A total amount of the first and second abrasive present in the oral composition are preferably greater than about 25%, even more preferably greater than about 30%.

In certain embodiments, the periodic oral composition comprises a first abrasive comprising silica and having an oil of absorption of less than about 90 cm$^3$/100 g and an Einlehner hardness of greater than about 5 mg loss per 100,000 revolutions. The periodic oral composition further comprises a second abrasive comprising silica and having an oil of absorption of greater than about 90 cm$^3$/100 g and an Einlehner hardness of less than about 5 mg loss per 100,000 revolutions. A ratio of the first abrasive to the second abrasive is about 1:1.6 to about 1.6:1. Further, a total amount of the first and second abrasives present in the oral composition is greater than about 25% by weight of the composition.

In certain embodiments, the periodic oral composition has a ratio of the first abrasive to the second abrasive that ranges from about 1:1.6 to about 1.6:1. In particular embodiments, the active ingredient comprises a non-ionic antibacterial ingredient, such as a halogenated diphenyl ether like triclosan, which will be discussed in more detail below. In some embodiments, the first abrasive has an oil of absorption of less than about 90 cm$^3$/100 g and an Einlehner hardness of greater than about 5 mg loss per 100,000 revolutions, and the second abrasive has an oil of absorption of greater than about 90 cm$^3$/100 g and an Einlehner hardness of less than about 5 mg loss per 100,000 revolutions.

The periodic oral care compositions described herein (both the primary and the periodic) may comprise an orally acceptable carrier. Conventional ingredients that can be used to form the carriers for oral care compositions are well known to the skilled artisan. The carrier can be a liquid, semi-solid, or solid phase. Oral compositions can be in the form of a dentifrice (including toothpastes, toothpowders, and prophylaxis pastes), confectioneries (including gums, beads and chews), film, paint-on gels, or any other form known to one of skill in the art where abrasives are employed. Selection of specific carrier components is dependant on the desired product form.

In certain preferred embodiments, the composition(s) are independently in the form of a dentifrice, where an exemplary carrier is substantially semi-solid or solid. The carrier can be aqueous, in which case the carrier preferably comprises about 5% to about 95% water. In other embodiments, the carrier is substantially non-aqueous. The carrier optionally comprises, for example, oral care active ingredients, surface active agents, such as surfactants, emulsifiers, and foam modulators, viscosity modifiers and thickeners, humectants, diluents, fillers, additional pH modifying agents, colorants, preservatives, solvents, and combinations thereof. It is understood that while general attributes of each of the above categories of materials may differ; there may be some common attributes and any given material may serve multiple purposes within two or more of such categories of materials. As recognized by one of skill in the art, the oral composition(s) optionally include other materials in addition to those components previously described, including for example, emollients, moisturizers, mouth feel agents and the like. Examples of suitable carriers for oral compositions are disclosed in U.S. Pat. Nos. 6,669,929, 6,379,654, and 4,894,220, the content of each of which are incorporated herein by reference.

The oral care active ingredients include for example, antibacterial active agents, anti-tartar agents, anti-caries agents, anti-inflammatory agents, anti-sensitivity agents, enzymes, nutrients, and the like. Active agents among those useful herein are also disclosed in U.S. Pat. Nos. 6,290,933 and 6,685,921, the contents of each of which are incorporated herein by reference.

Any suitable fluoride ion source may be present in either or both of the oral composition(s), such as those recited in U.S. Pat. No. 5,080,887, the contents of which are incorporated herein by reference. Sources of fluoride ions, acid phosphatases, and pyrophosphatase enzyme inhibitors, are well known in the art as anti-caries agents. Examples of such sources are inorganic metal and/or ammonium fluoride salts and compounds, such as, for example: sodium fluoride, potassium fluoride, ammonium fluoride, calcium fluoride; a copper fluoride, such as cuprous fluoride; zinc fluoride, barium fluoride; sodium silicafluoride, ammonium fluorosilicate, sodium fluorozirconate; and sodium monofluorophosphate, aluminum mono- and di-fluorophosphate, and fluorinated sodium calcium pyrophosphate. The fluoride source can also be an amine fluoride, such as olaflur (N'octadecyltrimethylendiamine-N,N,N'-tris(2-ethanol)-dihydrofluoride). Sodium fluoride, amine fluoride, stannous fluoride, sodium monofluorophosphate (MFP), and mixtures thereof, are preferred.

Either or both oral composition(s) optionally comprise an anticalculus component, such as one or more of the anticalculus components recited in U.S. Pat. No. 5,292,526, the contents of which are incorporated herein by reference. In various embodiments, the anti-calculus component includes one or more polyphosphates. The anti-calculus composition can include at least one wholly or partially neutralized alkali metal or ammonium tripolyphosphate or hexametaphosphate salt present in the oral composition at an effective anti-calculus amount. The anti-calculus component can also include at least one water soluble, linear, molecularly dehydrated polyphosphate salt effective in an anticalculus amount. The anti-calculus component can also include a mixture of potassium and sodium salts, at least one of which is present in an effective anti-calculus amount as a polyphosphate anti-calculus agent. Other useful anticalculus agents include polycarboxylate polymers and polyvinyl methyl ether/ maleic anhydride (PVM/ MA) copolymers, such as GANTREZ®.

All other substances or molecules known to be useful in oral care compositions may be included in either or both of the daily or the periodic compositions. For example, such additional molecules may include antibacterial agents, anti-plaque agents, desensitizing agents, anti-inflammation agents, colorants, thickeners, flavorants, surfactants, abrasives, anti-adhesion agents, an anti-caries agent, a sensate, and/or vitamins.

Other components that may be added to either or both composition include a stannous ion agent; triclosan; triclosan monophosphate; chlorhexidine; alexidine; hexetidine; sanguinarine; benzalkonium chloride; salicylanilide; domiphen bromide; cetylpyridinium chloride (CPC); tetradecylpyridinium chloride (TPC); N-tetradecyl-4-ethylpyridinium chloride (TDEPC); octenidine; delmopinol; octapinol; nisin; zinc ion agent; copper ion agent; essential oils; furanones; bacteriocins, ethyl lauroyl arginate, extracts of magnolia, a metal ion source, arginine bicarbonate, honokiol, magonol, ursolic acid, ursic acid, morin, extract of sea buckthorn, a peroxide, an enzyme, a Camellia extract, a flavonoid, a flavan, halogenated diphenyl ether, creatine, and propolis.

We claim:

1. A method of cleaning an oral surface, maintaining oral health and/or increasing oral health comprising:
   a. contacting an oral surface with a primary oral care composition at least once daily, and
   b. contacting the oral surface with a periodic oral care composition at least once within a period of about 42 days but less than once daily;
   wherein the periodic oral care composition but not the primary oral care composition comprises a first abrasive having an Einlehner hardness of greater than 5 mg loss per 100,000 revolutions and a second abrasive having an Einlehner hardness of less than about 5 mg loss per 100,000 revolutions,
   wherein a ratio of the first abrasive to the second abrasive ranges from about 1:1.6 to about 1.6:1,
   wherein the periodic oral composition has a pellicle cleaning ratio of greater than about 100 and a radioactive dentin abrasion of less than 200, and
   wherein the first abrasive and the second abrasive each comprised silica.

2. The method of claim 1, wherein (b) is accomplished by applying the periodic oral care composition of the oral surface with a brush.

3. The method of claim 1, wherein the primary oral care composition comprises an agent selected from an abrasive agent, an antibacterial agent, a plaque dispersion agent, an antiadhesion agent, an anticaries agent, a desensitizing agent, a flavorant, a colorant, and a sensate.

4. The method of claim 1, wherein the primary oral care composition comprises an agent selected from a stannous ion agent; triclosan; triclosan monophosphate; chlorhexidine; alexidine; hexetidine; sanguinarine; benzalkonium chloride; salicylanilide; domiphen bromide; cetylpyridinium chloride (CPC); tetradecylpyridinium chloride (TPC); N-tetradecyl-4-ethylpyridinium chloride (TDEPC); octenidine; delmopinol; octapinol; nisin; zinc ion agent; copper ion agent; essential oils; furanones; bacteriocins, ethyl lauroyl arginate, arginine bicarbonate, honokiol, magonol, ursolic acid, ursic acid, morin, a peroxide, an enzyme, a flavonoid, a flavan, halogenated diphenyl ether, creatine, and propolis.

5. The method of claim 1, wherein the oral surface is contacted to the primary oral care composition two to five times daily.

6. The method of claim 1, wherein the periodic oral composition has a radioactive dentin abrasion of less than about 175.

7. The method of claim 1, wherein the first abrasive of the periodic oral care composition has an oil of absorption of less than about 90 cm$^3$/100 g and the second abrasive has an oil of absorption of greater than about 90 cm$^3$/100 g.

8. The method of claim 1, wherein the first abrasive of the periodic oral care composition has a mean particle size of less than about 11 μm and the second abrasive has a mean particle size of greater than about 8 μm.

9. The method of claim 1, wherein the first abrasive of the periodic oral care composition is present in an amount of about 17% by weight of the periodic oral care composition and the second abrasive of the periodic oral care composition is present in an amount of about 17% by weight of the periodic oral care composition.

10. The method of claim 1, wherein a total amount of the first and second abrasives in the periodic oral care composition is greater than about 30% by weight of the composition.

11. The method of claim 1, wherein the first abrasive of the periodic oral care composition is present in an amount of about 13% to about 21% by weight and the second abrasive the periodic oral care composition is present in an amount of about 13% to about 21% by weight of the periodic oral care composition.

12. The method of claim 1, wherein the first abrasive and the second abrasive of the periodic oral care composition each comprise silica.

13. The method of claim 1, wherein the oral surface is contacted with the periodic oral care composition 4 to 18 times within a period of 42 days.

14. The method of claim 1, wherein the oral surface is contacted with the periodic oral care composition 6 times with a period of 42 days.

15. A method of cleaning an oral surface, maintaining oral health, and/or increasing oral health comprising
  a. contacting an oral surface with a primary oral care composition at least once daily, and
  b. contacting the oral surface with a periodic oral care composition at least once within a period of about 42 days but less than once daily;
  wherein the periodic oral care composition but not the primary oral care compostion comprises a first abrasive comprising silica, having an Einlehner hardness of greater than about 5 mg loss per 100,000 revolutions, and an oil of absorption of less than about 90 cm$^3$/100 g and a second abrasive comprising silica, having an Einlehner hardness of less than about 5 mg loss per 100,000 revolutions, and an oil of absorption of greater than about 90 cm$^3$/100 g, wherein the first abrasive is present in an amount of about 13% to about 21% by weight and the second abrasive is present in an amount of about 13% to about 21% by weight wherein the periodic oral composition has a pellicle cleaning ration of greater than about 100 and a radioactive dentin abrasion of less than about 200, and wherein the first abrasive and the second abrasive each comprise silica.

16. A method of cleaning an oral surface, maintaining oral health, and/or increasing oral health comprising
  a. contacting an oral surface with a primary oral care composition at least once daily, and
  b. contacting the oral surface with a periodic oral care composition at least once within a period of about 42 days but less than once daily;
  wherein the periodic oral care composition but not the primary oral care composition comprises an first abrasive comprising silica and having an oil of absorption of less than about 90 cm$^3$/100 g and an Einlehner hardness of greater than about 5 mg loss per 100,000 revolutions, and a second abrasive comprising silica and having an oil of absorption of greater than about 90 cm$^3$/100 g and an Einlehner hardness of less than about 5 mg loss per 100,000 revolutions, wherein a ratio of the first abrasive to the second abrasive is about 1:1.6 to about 1.6:1, and a total the first and second abrasives present in the oral composition is greater than about 25% by weight of the composition, wherein the oral composition has a pellicle cleaning ratio of greater than about 100 and a radioactive dentin abrasion of less than about 200 and wherein the first abrasive and the second abrasive each comprise silica.

* * * * *